United States Patent [19]

Martel et al.

[11] 4,401,601
[45] Aug. 30, 1983

[54] NOVEL PROCESS FOR THE PREPARATION OF TETRA-SUBSTITUTED CYCLOPROPANE COMPOUNDS

[75] Inventors: Jacques Martel, Bondy; Jean Tessier, Vincennes; Jean-Pierre Demoute, Montreuil-sous-Bois, all of France

[73] Assignee: Roussel Uclaf, Paris, France

[21] Appl. No.: 246,172

[22] Filed: Mar. 23, 1981

[30] Foreign Application Priority Data

Mar. 28, 1980 [FR] France ............................. 80 06979

[51] Int. Cl.$^3$ .................... C07C 121/46; C07C 69/74; C07C 61/04
[52] U.S. Cl. ................................ 260/464; 260/465 R; 560/11; 560/117; 560/118; 560/124; 562/500; 562/499; 562/506
[58] Field of Search ....................... 260/464; 560/124; 562/506

[56] References Cited

U.S. PATENT DOCUMENTS

| | | | |
|---|---|---|---|
| 3,445,499 | 5/1969 | Martel et al. | 260/464 |
| 3,567,780 | 3/1971 | Martel et al. | 560/122 X |
| 3,711,555 | 1/1973 | Martel et al. | 260/544 L X |
| 3,786,052 | 1/1974 | Martel et al. | 260/544 L X |

OTHER PUBLICATIONS

Yanovskaya, et al., Russian Chemical Reviews, vol. 44, No. 2, (1975), pp. 154–169.

Primary Examiner—Joseph Paul Brust
Attorney, Agent, or Firm—Hammond, Littell, Weissenberger & Muserlian

[57] ABSTRACT

A process for the preparation of tetrasubstituted cyclopropane compounds of the formula

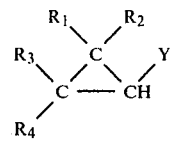

wherein Y is selected from the group consisting of —CN and —COOR, R is selected from the group consisting of hydrogen and alkyl of 1 to 6 carbon atoms and $R_1$, $R_2$, $R_3$ and $R_4$ are individually selected from alkyl of 1 to 4 carbon atoms or $R_1$ and $R_2$ or $R_3$ and $R_4$ together with the carbon atoms to which they are attached form a carbon homocycle of 3 to 6 carbon atoms with the 2 substituents not forming the ring being alkyl of 1 to 4 carbon atoms or $R_1$ and $R_2$ on the one hand and $R_3$ and $R_4$ on the other together with the carbon atom to which they are attached form a carbon homocycle of 3 to 6 carbon atoms which are useful intermediates for the preparation of insecticidal esters and novel intermediates.

6 Claims, No Drawings

NOVEL PROCESS FOR THE PREPARATION OF TETRA-SUBSTITUTED CYCLOPROPANE COMPOUNDS

STATE OF THE ART

U.S. Pat. No. 3,445,499 describes the following reactions:

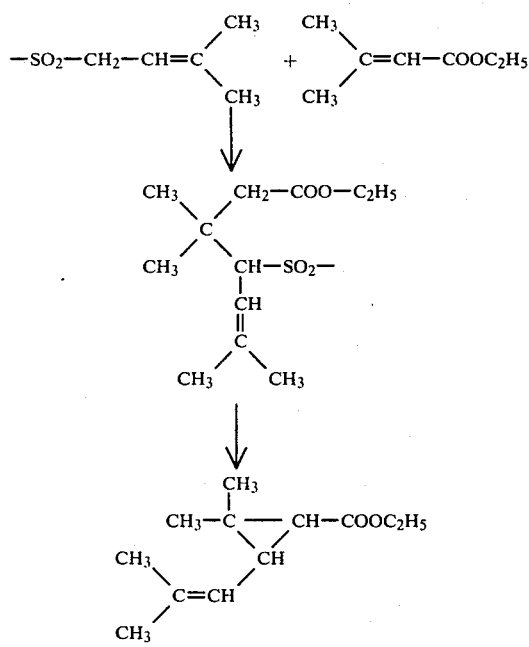

However, the aryl sulfone is different and the products of the process are different than the process of the invention.

Russian Chemical Reviews, Vol. 44 No. 2 (1975), p. 154 to 169 describes the preparation of cyclopropane derivatives using sulfur, sulfoxy or sulfonic derivatives but the derivatives are not the type used in the process of the invention. Moreover, the reference does not react an aryl sulfone with an alkyl acrylate.

OBJECTS OF THE INVENTION

It is an object of the invention to provide a novel process for the preparation of tetrasubstituted cyclopropane-compounds of formula I.

It is another object of the invention to provide novel intermediate compounds.

These and other objects and advantages of the invention will become obvious from the following detailed description.

THE INVENTION

The novel process of the invention for the preparation of tetrasubstituted cyclopropane compounds of the formula

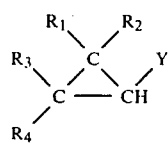

wherein Y is selected from the group consisting of —CN and —COOR, R is selected from the group consisting of hydrogen and alkyl of 1 to 6 carbon atoms and $R_1$, $R_2$, $R_3$ and $R_4$ are individually selected from alkyl of 1 to 4 carbon atoms or $R_1$ and $R_2$ or $R_3$ and $R_4$ together with the carbon atom to which they are attached form a carbon homocycle of 3 to 6 carbon atoms with the 2 substituents not forming the ring being alkyl of 1 to 4 carbon atoms or $R_1$ and $R_2$ on the one hand and $R_3$ and $R_4$ on the other together with the carbon atoms to which they are attached form a carbon homocycle of 3 to 6 carbon atoms comprising reacting a sulfone of the formula

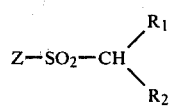

wherein Z is an aromatic group and $R_1$ and $R_2$ have the above definition at a low temperature with a strong base in a polar solvent and reacting the resulting product at a low temperature with a compound of the formula

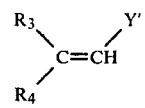

wherein Y' is selected from the group consisting of —CN and —COOR', R' is alkyl of 1 to 6 carbon atoms and $R_3$ and $R_4$ have the above definitions to obtain a compound of the formula

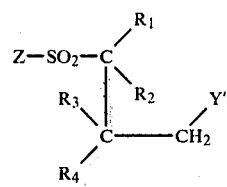

and reacting the latter in the presence of a strong base in a polar solvent at a low temperature and then heating the mixture to obtain a compound of the formula

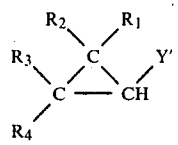

and subjecting the latter, if desired, to hydrolysis in the presence of a basic agent to obtain a compound of the formula

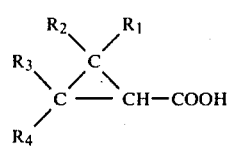

When Y is —COOR, R is hydrogen or alkyl of 1 to 6 carbon atoms such as methyl, ethyl, n-propyl, isopropyl and branched or straight chain butyl, pentyl or hexyl. $R_1$, $R_2$, $R_3$ and $R_4$ may individually be alkyl of 1 to 4 carbon atoms such as methyl, ethyl, propyl, isopropyl and branched or straight chain butyl. $R_1$ and $R_2$ or $R_3$ and $R_4$ together with the carbon atoms to which they are attached may form a cycloalkyl such as cyclopropyl, cyclobutyl, cyclopentyl or cyclohexyl with the other Rs being alkyl of 1 to 4 carbon atoms or both $R_1$ and $R_2$ and $R_3$ and $R_4$ together with the carbon atoms to which they are attached may form cycloalkyl such as cyclopropyl, cyclobutyl, cyclopentyl or cyclohexyl. Examples of Z are monocyclic aryl such as phenyl, tolyl and xylyl.

In the compounds of formula II, when Y' is —COOR', R' may be methyl, ethyl, propyl, isopropyl or branched or straight chain butyl, pentyl or hexyl. In a preferred embodiment of the invention, the intermediate of formula IV is not isolated. Preferably, $R_1$, $R_2$, $R_3$ and $R_4$ are all methyl.

In a preferred mode of the process of the invention, the reaction of the compounds of formulae II and III is between −90° to 0° C. and examples of the polar solvents are dimethylsulfoxide, dimethoxyethane, dimethylformamide, tetrahydrofuran, hexamethylphosphorotriamide, monocyclic aromatic hydrocarbons, cycloalkanes and mixtures of the said solvents. The strong base is preferably an alkali metal alcoholate, alkali metal amide, alkali metal hydride, aryllithiums and alkyllithiums.

The compound of formula IV is reacted in the presence of a strong base such as alkali metal alcoholates, alkali metal amides, alkali metal hydrides, aryllithiums or alkyllithiums in a polar organic solvent such as those discussed above at −90° to 0° C. and the basic hydrolysis agent is preferably an alkali metal hydroxide and the hydrolysis is effected in a water-miscible solvent, preferably an alkanol.

The process of the invention has the advantage of using readily available reactants and obtains in a few steps tetra-substituted cyclopropane carboxylic acid derivatives, especially tetramethyl cyclopropane carboxylic acids and their lower alkyl esters which are intermediates for insecticidally active esters such as 3-allyl-2-methyl-4-oxo-2-cyclopentenyl 2,2,3-tetramethyl-cyclopropane carboxylate or 3-allyl-2-methyl-4-oxo-2-cyclopentenyl 2,2,3-trimethyl-3-ethyl-cyclopropane-carboxylate.

The first step of the process presents a particularly unexpected character since it is well known to those skilled in the art that the addition of a highly hindered acrylate of formula II to an equally hindered sulfone of formula III is very difficult to realize. On the contrary to what one would be led to believe, the reaction of the compounds of formulae II and III is effected with good yields.

The novel intermediate compounds of the invention are the compounds of formula IV, especially methyl 4-(p-tolylsulfonyl)-4,3,3-trimethyl-pentanoate and 4-(p-tolylsulfonyl)-4,3,3,-trimethyl-pentanenitrile.

In the following examples there are described several preferred embodiments to illustrate the invention. However, it should be understood that the invention is not intended to be limited to the specific embodiments.

EXAMPLE 1

2,2,3,3,-tetramethyl-cyclopropane-1-carboxylic acid

STEP A: Methyl 4-p-tolylsulfonyl-4,3,3-trimethyl-pentanoate 5 ml of a cyclohexane solution of 1.75M butyllithium and 3 ml of anhydrous hexamethylphosphorotriamide were added under an inert atmosphere at −30° to −40° C. with stirring to a mixture of 1.737 g of p-tolylisopropylsulfone and 5 ml of tetrahydrofuran and the mixture was stirred at −30° to −40° C. for 15 minutes. A solution of 1 g of methyl dimethylacrylate in 5 ml of tetrahydrofuran was added over 10 minutes at −60° to −70° C. to the mixture and the mixture was stirred at the said temperature for 30 minutes and was then poured into iced aqueous saturated monosodium phosphate solution. The mixture was extracted with benzene and the organic phase was dried and evaporated to dryness under reduced pressure to obtain a residue of 2.81 g. The latter was chromatographed over silica gel and was eluted with a 1-1 petroleum ether (b.p.=40–70° C.) -ether mixture to obtain 1.5 g of methyl 4-p-tolylsulfonyl-4,3,3-trimethyl-pentanoate melting at 90° C. After crystallization from isopropyl ether, the 1.125 g of pure product melted at 90–92° C.

NMR Spectrum (deuterochloroform):

Peaks at 1.27 and 1.36 ppm (hydrogens of 3- and 4-methyls); at 2.88 ppm (2-hydrogens); at 3.7 ppm (hydrogens of —COOCH$_3$); at 7.27 to 7.85 ppm (aromatic hydrogens.).

STEP B: Methyl 2,2,3,3-tetramethyl-cyclopropane-1-carboxylate 2.11 ml of a cyclohexane solution of 1.75M of butyllithium were added at −30° to −40° C. to a mixture of 0.58 ml of diisopropylamine and 2 ml of tetrahydrofuran and after 15 minutes of contact, the solution was cooled to −60° to −70° C. after which 1.048 g of the product of Step A was added thereto over 10 minutes. The mixture was stirred at −60° to −70° C. for 10 minutes and the temperature was allowed to rise to 20° to 25° C. After one hour of contact, the mixture was poured into iced aqueous saturated monosodium phosphate solution and the mixture was extracted with n-pentane. The organic phase was dried and evaporated to dryness under reduced pressure to obtain a residue of 0.749 g. The latter was chromatographed over silica gel and was eluted with a 7-3 petroleum ether-ether mixture to obtain 0.293 g of methyl 2,2,3,3-tetramethylcyclopropane-1-carboxylate in the form of a colorless oil with a boiling point of 78° C. at 32 mmHg.

NMR Spectrum (deuterochloroform):

Peaks at 1.18 and 1.25 ppm (hydrogens of methyls fixed on cyclopropane); at 3.62 ppm (hydrogens of —COOCH$_3$).

STEP C: 2,2,3,3-tetramethyl-cyclopropane-1-carboxylic acid

A mixture of 4.535 g of the product of Step B, 55 ml of methanol and 25 ml of N sodium hydroxide solution was refluxed with vigorous stirring for 24 hours and was then cooled to room temperature. The basic medium was extracted with methylene chloride and was then acidified to a pH of 1 by addition of concentrated hydrochloric acid. The mixture was extracted with methylene chloride and the organic phase was dried and evaporated to dryness under reduced pressure to obtain 4.13 g of residue which was crystallized from isopropyl ether to obtain 3.72 g of 2,2,3,3-tetramethyl-cyclopropane-1-carboxylic acid melting at 122° C.

NMR Spectrum (deuterochloroform):

Peaks at 1.18 and 1.25 ppm (hydrogens of methyls).

EXAMPLE 2

2,2,3,3-tetramethyl-cyclopropane-1-carboxylic acid

STEP A:

4-p-tolylsulfonyl-4,3,3-trimethyl-pentanenitrile 3.81 ml of a cyclohexane solution of 1.75M of butyllithium were added at −30° to −40° C. to a mixture of 1.05 ml of diisopropylamine and 4 ml of tetrahydrofuran and the mixture was stirred for 10 minutes and was then cooled to −60° to −70° C. Then 1.22 g of p-tolyl isopropylsulfone were added to the mixture which after 15 minutes of contact was poured over 10 minutes under an inert atmosphere into a solution of 0.5 g of dimethylacrylonitrile and 4 ml of tetrahydrofuran at −60° to −70° C. The mixture was stirred for 30 minutes at −60° to −70° C. and was then poured into an aqueous saturated monosodium phosphate solution. The mixture was extracted with benzene and the organic phase was dried and evaporated to dryness. The residue was crystallized from isopropyl ether to obtain 0.740 g of 4-p-tolylsulfonyl-4,3,3,-trimethyl-pentanenitrile melting at 126° C.

NMR Spectrum (deuterochloroform):

Peaks at 1.27 and 1.38 ppm (hydrogens of 3- and 4-methyls); at 3.0 ppm (2-hydrogens); at 2.42 ppm (hydrogens of —$CH_3$ of tolyl); at 7.28 to 7.83 ppm (aromatic hydrogens).

U.V. Spectrum (ethanol):

Max. at 228 nm: $E_1^1 = 517$.

STEP B:

2,2,3,3,-tetramethyl-cyclopropane-carbonitrile 9.15 ml of a cyclohexane solution of 1.75M of butyllithium were added with stirring under an inert atmosphere at −30° to −40° C. to a mixture of 2.49 ml of diisopropylamine and 5 ml of tetrahydrofuran and after 10 minutes of contact, the mixture was cooled to −60° to −70° C. A mixture of 4.068 g of 4-tolyl sulfonyl-4,3,3-trimethyl-pentanenitrile in 15 ml of tetrahydrofuran were added to the mixture over 5 minutes and the mixture was stirred at −60° to −70° C. for 10 minutes after which the temperature was allowed to rise to 20° to 25° C. The mixture was stirred for one hour and was then poured into an iced aqueous saturated monosodium phosphate solution. The mixture was extracted with n-pentane and the organic phase was dried and evaporated to dryness under reduced pressure. The residue was distilled under reduced pressure to obtain 1.064 g of pure 2,2,3,3-tetramethyl-cyclopropane-carbonitrile with a boiling point of 58°-60° C. at 12-14 mm Hg and a melting point of 17° C.

NMR Spectrum (deuterochloroform):

Peaks at 1.19 and 1.25 ppm (hydrogens of methyls); at 0.94 ppm (1-hydrogen).

STEP C:

2,2,3,3-tetramethyl-cyclopropane-1-carboxylic acid

A mixture of 577 mg of the product of Step B and 100 ml of aqueous 5 N sodium hydroxide solution and 20 ml of methanol was refluxed for 144 hours and was then cooled. The mixture was extracted with methylene chloride and the aqueous phase was acidified to a pH of 1 with concentrated hydrochloric acid. The mixture was extracted with methylene chloride and the organic phase was dried and evaporated to dryness under reduced pressure to obtain 500 mg of 2,2,3,3-tetramethyl-cyclopropane-1-carboxylic acid melting at 120° C.

Various modifications of the products and process of the invention may be made without departing from the spirit or scope thereof and it is to be understood that the invention is intended to be limited only as defined in the appended claims.

What we claim:

1. A process for the preparation of tetrasubstituted cyclopropane compounds of the formula

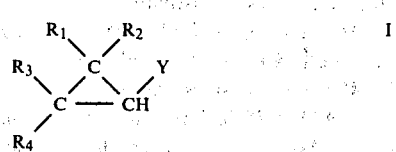

wherein Y is selected from the group consisting of —CN and —COOR, R is alkyl of 1 to 6 carbon atoms and $R_1$, $R_2$, $R_3$ and $R_4$ are individually selected from alkyl of 1 to 4 carbon atoms or $R_1$ and $R_2$ or $R_3$ and $R_4$ together with the carbon atoms to which they are attached form a carbon homocycle of 3 to 6 carbon atoms with the 2 substituents not forming the ring being alkyl of 1 to 4 carbon atoms or $R_1$ and $R_2$ on the one hand and $R_3$ and $R_4$ on the other together with the carbon atoms to which they are attached form a carbon homocycle of 3 to 6 carbon atoms comprising reacting a sulfone of the formula

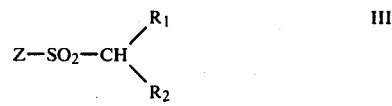

wherein Z is a monocyclic hydrocarbon aromatic group and $R_1$ and $R_2$ have the above definition at a temperature of −90° to 0° C. with a strong base selected from the group consisting of alkali metal alcoholates, alkali metal amides, alkali metal hydrides, aryllithiums and alkyllithiums in a polar solvent and reacting the resulting product at a temperature of −90° to 0° C. with a compound of the formula

wherein Y, $R_3$ and $R_4$ have the above definition to obtain a compound of the formula

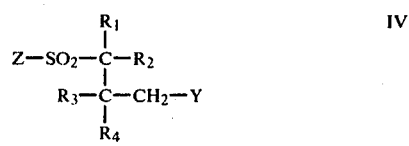

and reacting the latter in the presence of a strong base selected from the group consisting of alkali metal alcoholates, alkali metal amides, alkali metal hydrides, aryllithiums and alkyllithiums in a polar solvent at a temperature of −90° to 0° C. and then allowing the mixture to rise to about room temperature to obtain a compound of the formula

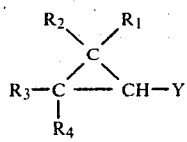

2. The process of claim 1 wherein the compound of formula IV is not isolated.

3. The process of claim 1 wherein $R_1$, $R_2$, $R_3$ and $R_4$ are methyl.

4. The process of claim 1 wherein the polar organic solvent is selected from the group consisting of dimethyl-sulfoxide, dimethoxyethane, dimethylformamide, tetrahydrofuran, hexamethylphosphorotriamide, monocyclic aromatic hydrocarbons, cycloalkanes and mixtures of the said solvents.

5. The process of claim 1 wherein the product of formula I is reacted with a base in a water-miscible solvent and then an acid to obtain a compound of the formula

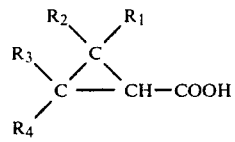

6. The process of claim 5 wherein the solvent is an alkanol.

* * * * *